(12) United States Patent
Hatzis et al.

(10) Patent No.: US 10,420,667 B2
(45) Date of Patent: Sep. 24, 2019

(54) METHOD AND FOOT SUPPORT DEVICE FOR TREATING PLANTAR FASCIITIS IN THE FOOT OF A PATIENT WHILE THE PATIENT IS MOBILE

(71) Applicant: REBEL INNOVATIONS, INC., Stamford, CT (US)

(72) Inventors: Thomas V Hatzis, Stamford, CT (US); Stanley Wadolowski, Stamford, CT (US); Scott Axelrod, Wakefield, RI (US); J. Michael Cantore, Jr., Stamford, CT (US)

(73) Assignee: REBEL INNOVATIONS, INC., Stamford, CT (US)

( * ) Notice: Subject to any disclaimer, the term of this patent is extended or adjusted under 35 U.S.C. 154(b) by 187 days.

(21) Appl. No.: 15/189,499

(22) Filed: Jun. 22, 2016

(65) Prior Publication Data
US 2016/0296358 A1 Oct. 13, 2016

Related U.S. Application Data

(63) Continuation-in-part of application No. 13/545,976, filed on Jul. 10, 2012, now Pat. No. 9,452,076.

(51) Int. Cl.
*A61F 5/01* (2006.01)

(52) U.S. Cl.
CPC .......... *A61F 5/0113* (2013.01); *A61F 5/0123* (2013.01); *A61F 5/0127* (2013.01)

(58) Field of Classification Search
CPC ..... A61F 5/0113; A61F 5/0116; A61F 5/0111; A61F 5/0127; A61F 5/0195; A63B 21/143; A63B 21/1449; A63B 23/08; A63B 23/085
USPC .......... 602/23, 26–29; 128/882; 482/124, 79
See application file for complete search history.

(56) References Cited

U.S. PATENT DOCUMENTS

| | | | |
|---|---|---|---|
| 4,930,767 A * | 6/1990 | Hamm | A63B 21/0552 482/124 |
| 5,399,155 A | 3/1995 | Strassburg et al. | |
| 7,175,574 B2 * | 2/2007 | Carmel | A63B 21/0004 482/124 |
| 7,753,864 B2 | 7/2010 | Beckwith et al. | |
| 9,452,076 B2 * | 9/2016 | Hatzis | A61F 5/0127 |
| 2008/0306422 A1 * | 12/2008 | McChesney | A61F 5/0111 602/26 |

* cited by examiner

*Primary Examiner* — Kari K Rodriquez
(74) *Attorney, Agent, or Firm* — Eugene Lieberstein

(57) ABSTRACT

The invention is directed to a method and foot support device for dynamically treating plantar fasciitis in the foot of a patient while enabling patient mobility. The method comprises applying tension to the ball of the foot via a strap held in tension by extending the strap to form a continuous loop, from opposite sides of the knee in the leg of the foot in treatment through an opening in a channel guide member oriented relative to the ball of the foot, with the strap connected at opposite ends thereof to the opposite sides of the knee in alignment with the rotatable joint of the knee and controlling dorsiflexion of the plantar fascia while the patient is mobile by slidably adjusting the position of the strap within the channel guide member in response to the mobility of the patient.

6 Claims, 12 Drawing Sheets

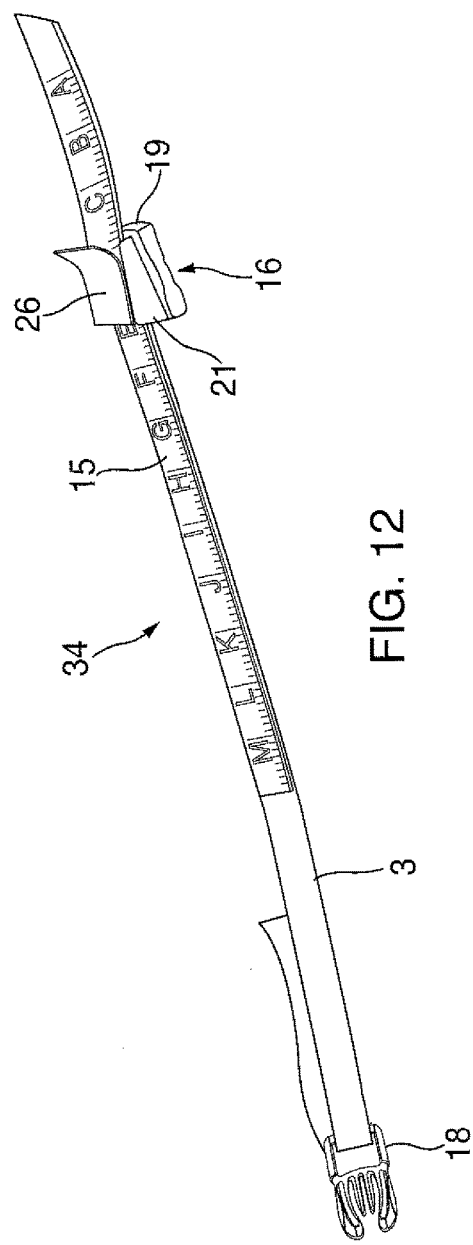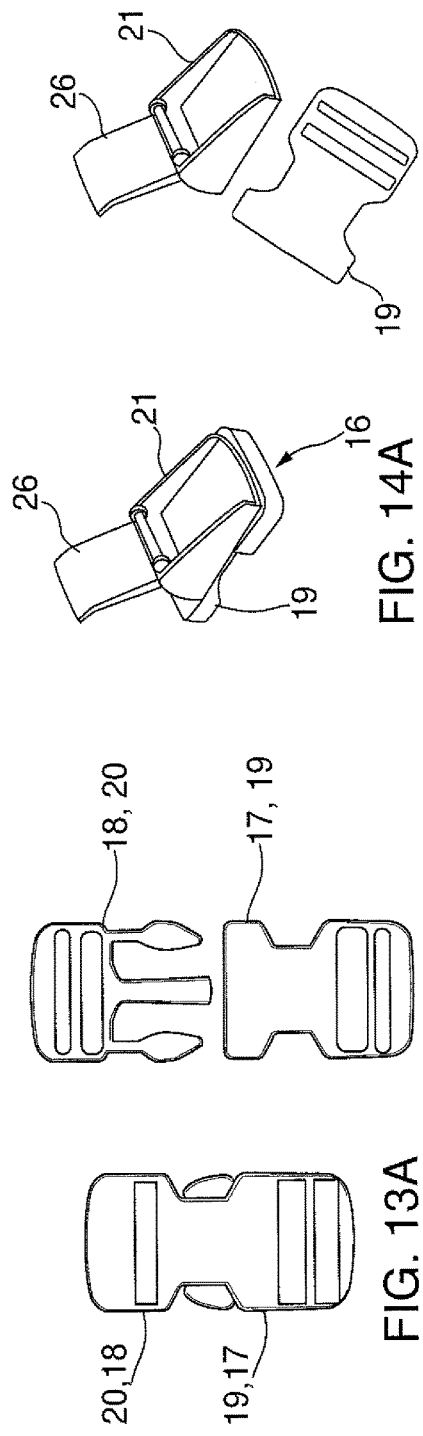

METHOD AND FOOT SUPPORT DEVICE FOR TREATING PLANTAR FASCIITIS IN THE FOOT OF A PATIENT WHILE THE PATIENT IS MOBILE

This invention is a continuation in part of Ser. No. 13/545,976 filed on Jul. 10, 2012, the disclosure of which is herein incorporated in its entirety by reference, and relates to a method and foot support device for treating plantar fasciitis in the foot of a patient by controllably maintaining dorsiflexion of the plantar fascia while at the same time permitting the patient to be mobile.

FIELD OF THE INVENTION

Background of the Invention

The human foot and ankle contain 26 bones and more than 100 muscles, tendons, and ligaments. This complex structure receives the impact of each step experienced by an individual.

One source of heel pain commonly observed is due to a condition known as recalcitrant plantar fasciitis. Plantar fasciitis occurs in the plantar fascia, a fibrous membrane disposed longitudinally across the bottom of the foot. The plantar fascia is attached at the heel bone. The plantar fascia becomes broader and thinner as it extends longitudinally across the bottom of the foot, eventually dividing near the heads of the metatarsal bones into five processes, one for each of the five toes. The strongest ligament in the body, the plantar fascia's purpose is to protect the softer muscles and tissues of the bottom of the foot from injury, as well as to help maintain the integrity of the foot structure itself.

If the fascia becomes stretched or strained, the arch area becomes tender and swollen as well as the area about the heel bone. This inflammation is called plantar fasciitis and is typically painful from the heel throughout the arch up into the Achilles tendon. Patients suffering from this condition usually have relatively tight and inflexible heel cords, sometimes referred to as Achilles tendon tightness. When the heel cord is tight, it causes compensation in the foot with over pronation of the foot during weight bearing. The pain is consistently worse when you first get up in the morning and at the end of the day. The pain usually lurks in the heel pad and may include the arch ligament.

Plantar fasciitis is often caused by contracture of the Achilles tendon and the plantar fascia, which can occur at night during sleep, or during daytime inactivity. The Achilles tendon, the strongest and thickest tendon in the human body, begins at or about the middle of the posterior side of the leg extending downward towards the heel, narrowing as it progresses towards its point of insertion at the posterior surface of the os calcis. When an individual is standing, walking, running, or even sitting in a position in which the feet are in contact with the floor or other surface, both the plantar fascia and the Achilles tendon are extended to varying degrees depending of course on the nature and intensity of the activity. During sleep, an individual has a natural tendency to plantar flex the ankle joint beyond the position, which is normal during walking, standing, or sitting with one's feet on the floor. Plantarflexion is when the bottom of the foot is extended so as to form an angle with the lower leg of greater than 90 degrees, i.e., extend such that the forefoot moves away from the body. Dorsiflexion is the opposite motion, when the foot is moved to a position in which the bottom of the foot forms an angle with the lower leg of less than 90 degrees, i.e., such that the top of the foot moves toward the body.

Another condition, Achilles tendonitis can result from overuse of the tendon in sports activities, and can also result from a number of inflammatory diseases, of which rheumatoid arthritis is one.

Plantar fasciitis has been heretofore treated with the foot undergoing treatment held essentially immobile. One common treatment of plantar fasciitis with the foot held immobile is to use a night splint. The night splint is a static device which typically consists, essentially, of a boot-like structure, which is strapped to a patient's lower leg and foot, holding the foot in a fixed position relative to the lower leg so that the leg does not move and with the ankle joint in slight dorsiflexion so that both the plantar fascia and the Achilles tendon are slightly extended and are not allowed to contract during the night. Although the night splint device is somewhat beneficial in the treatment of plantar fasciitis it is uncomfortable and limits mobility to the wearer and accordingly, the duration of treatment is limited.

Other static foot support devices such as braces and splints are known for maintaining the plantar fascia of the foot in a neutral to slight dorsiflexion under application of static tension. One such device is taught in U.S. Pat. No. 7,753,864 (Beckwith et al.) which includes (a) a calf strap removably engageable to the calf of a leg; (b) a foot assembly removably engageable to the foot of the leg such that when the device is worn the assembly can be positioned proximate to the ball of the foot intermediate to the midfoot and forefoot areas of the foot to secure it to the foot; and (c) a substantially inelastic tension member connectable between the calf strap and the foot assembly in a tensioned manner such that when the device is worn plantarflexion of the ankle is limited which in turn is able to keep the plantar surface of the foot held in a neutral to slight dorsiflexion. Once again, this device is a static device which does not permit the patient to be mobile while undergoing treatment and the duration of treatment is relatively limited.

An additional disadvantage of the calf strap configuration in Beckwith et al. is that the calf muscle receives the tension force which leads to discomfort for the user which is one reason use of the foot support device is limited to relatively short time durations. Another disadvantage of a calf strap configuration is that it requires the calf to be connected to the foot assembly which generates a downward force on the calf and prevents the user from making lateral adjustments in tension.

Currently there is no foot support device commercially available which can controllably maintain dorsiflexion of the plantar fascia while at the same time permit the patient to be mobile, other than Strassburg Sock U.S. Pat. No. 5,399,155 i.e., move the foot while undergoing treatment and walk. However, the Strassburg configuration requires the pulling on the toes in addition to tight restriction on the leg which may impact circulation on the leg. Therefore Strassburg is contrary to the concept and arrangement of structural elements in the subject invention.

What is therefore desired, is a device which functions dynamically, not statically and is able to control dorsiflexion of the plantar fascia while at the same time allowing the patient to be mobile and to move the leg while undergoing treatment. This results in substantially increased patient comfort and allows the duration of medical treatment to be substantially longer which, in turn, alleviates plantar fasciitis in a much shorter duration of time as compared to the use of conventional static devices.

SUMMARY OF THE INVENTION

A method has been discovered in accordance with the present invention for dynamically treating plantar fasciitis which permits patient mobility comprising the steps of applying tension to the ball of the foot via a strap held in tension by extending the strap to form a continuous loop, from opposite sides of the knee in the leg of said foot in alignment with the rotatable axis of the knee, through an opening in a channel guide member oriented relative to the ball of the foot and controlling dorsiflexion of the plantar fascia while the patient is mobile by slidably adjusting the position of the strap within the channel guide member in response to the mobility of the patient while the foot is maintained in constant dorsiflexion.

The present invention is also directed to a foot support device, adapted for attachment to a leg of a patient, for dynamically treating plantar fasciitis in a foot in said leg of said patient by controlling and maintaining dorsiflexion of the plantar fascia even if the patient is mobile during treatment, with the foot support device comprising:

a foot assembly comprising a sock, adapted for placement over the foot in said leg to undergo treatment, and a guide member affixed to the sock proximate the ball of the foot with said guide member having an opening extending therethrough;

a knee assembly comprising a first and second adjustable strap in a relationship above and below the kneecap of the knee in said leg, and a material section interconnecting the first adjustable strap to the second adjustable strap such that upon attachment of the foot support device to said leg the knee assembly forms a brace for the knee which engages and surrounds the knee. A knee assembly comprised of flexible material with a securing adjustment strap at top of the knee assembly which is attached by velcro and a securing adjustment strap at the bottom of the knee assembly which is attached by velcro.

a tension assembly comprising a tension strap having open ends with the tension strap able to slide and extend through the opening in said guide member;

coupling members for interconnecting the open ends of said tension strap to the knee assembly, at points of connection to the knee assembly located on opposite sides of the knee in substantial alignment with the rotatable joint of the knee, such that the tension strap is held in tension with the tension strap forming a continuous loop extending from one side of the knee assembly through the passageway in said guide member under said ball of the foot to the opposite side of said knee assembly; and means for adjusting tension in said tension strap such that consistent and uniform pressure is applied to the ball of the foot undergoing treatment while allowing the strap member, held in tension, to slide and adjust position within the guide member when the patient is mobile and moves the leg during treatment.

BRIEF DESCRIPTION OF THE DRAWINGS

FIG. 12 is a view in elevation of a portion of the tension assembly in the foot support device shown in FIG. 9 showing the clamp assembly for adjusting tension in the tension strap in the tension assembly;

FIG. 13A is a top view of a pair of coupling members for coupling the tension assembly to the knee assembly in the foot support device shown in FIG. 9 with the coupling members in the pair shown engaged to each other;

FIG. 13B is another top view of a pair of coupling members for coupling the tension assembly to the knee assembly in the foot support device shown in FIG. 9 with the coupling members in the pair shown disengaged from one another;

FIG. 14A is a perspective view of the clamp assembly in the foot support device shown in FIGS. 9 and 12 for adjusting tension in the tension strap in the tension assembly; and FIG. 14B is an exploded perspective view of the clamp assembly shown in FIG. 14A.

DETAILED DESCRIPTION OF THE FIRST EMBODIMENT OF THE INVENTION

Figure 1:
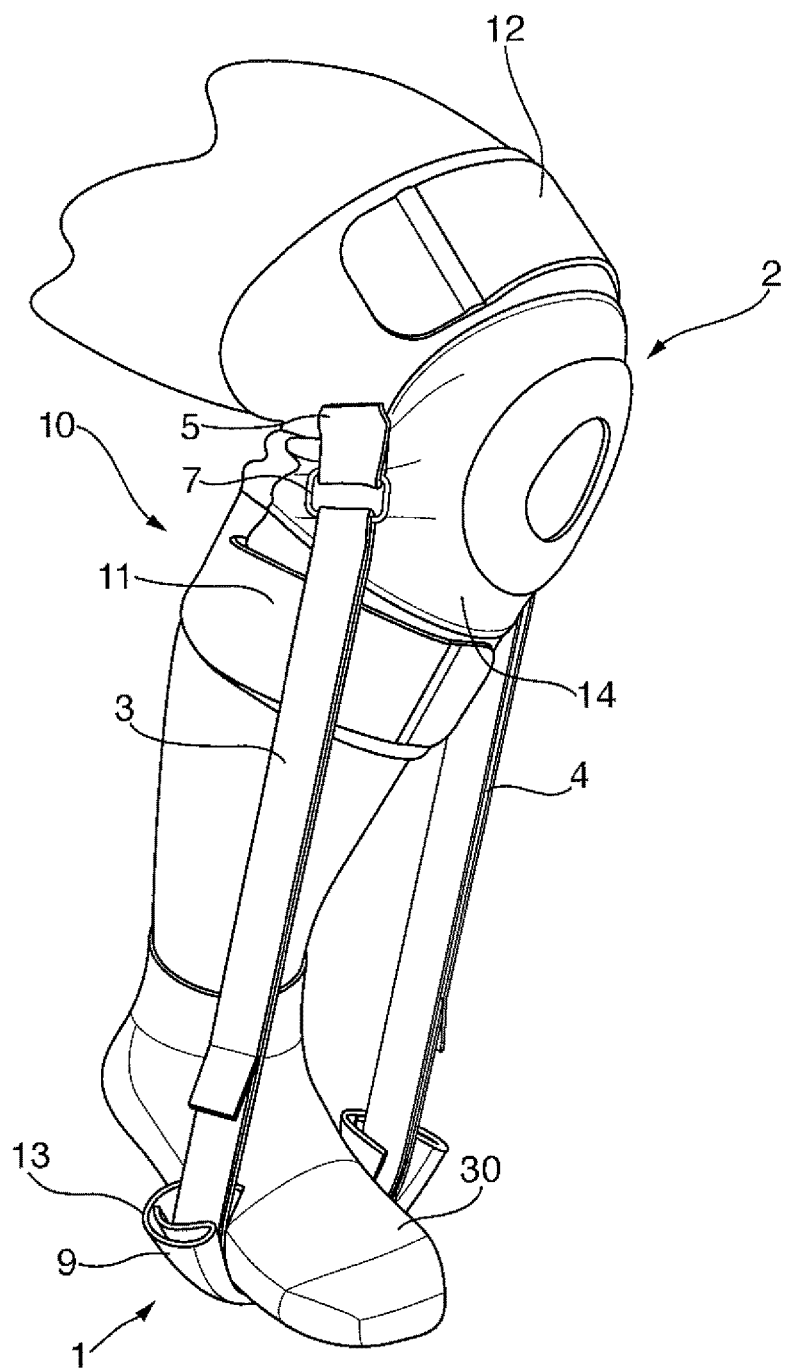
FIG. 1 illustrates a first embodiment of the foot support device of the present invention shown in perspective and attached to a leg of a patient.
Figure 2:
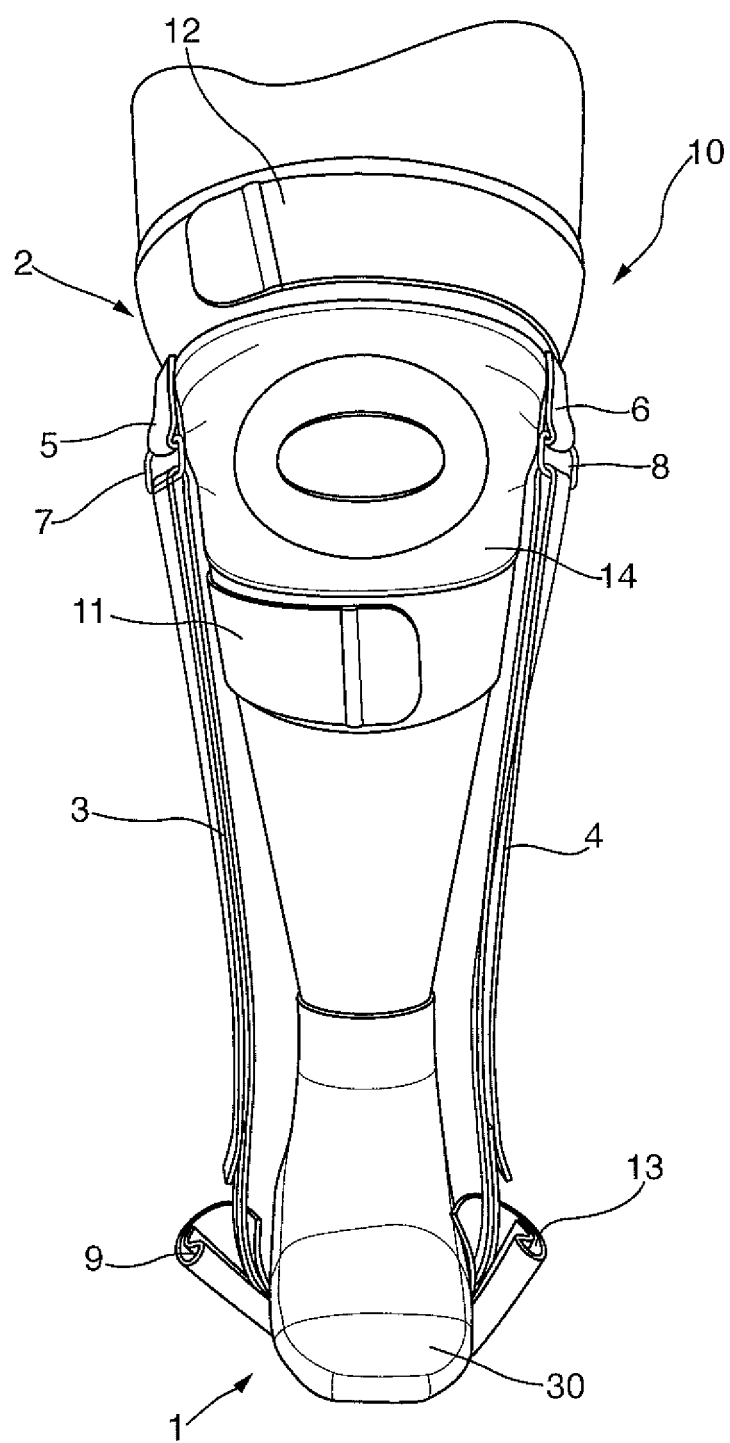
FIG. 2 is another perspective view of the first embodiment of the invention shown in FIG. 1 with the foot support device shown rotated ninety degrees from the position in FIG. 1.
Figure 10:
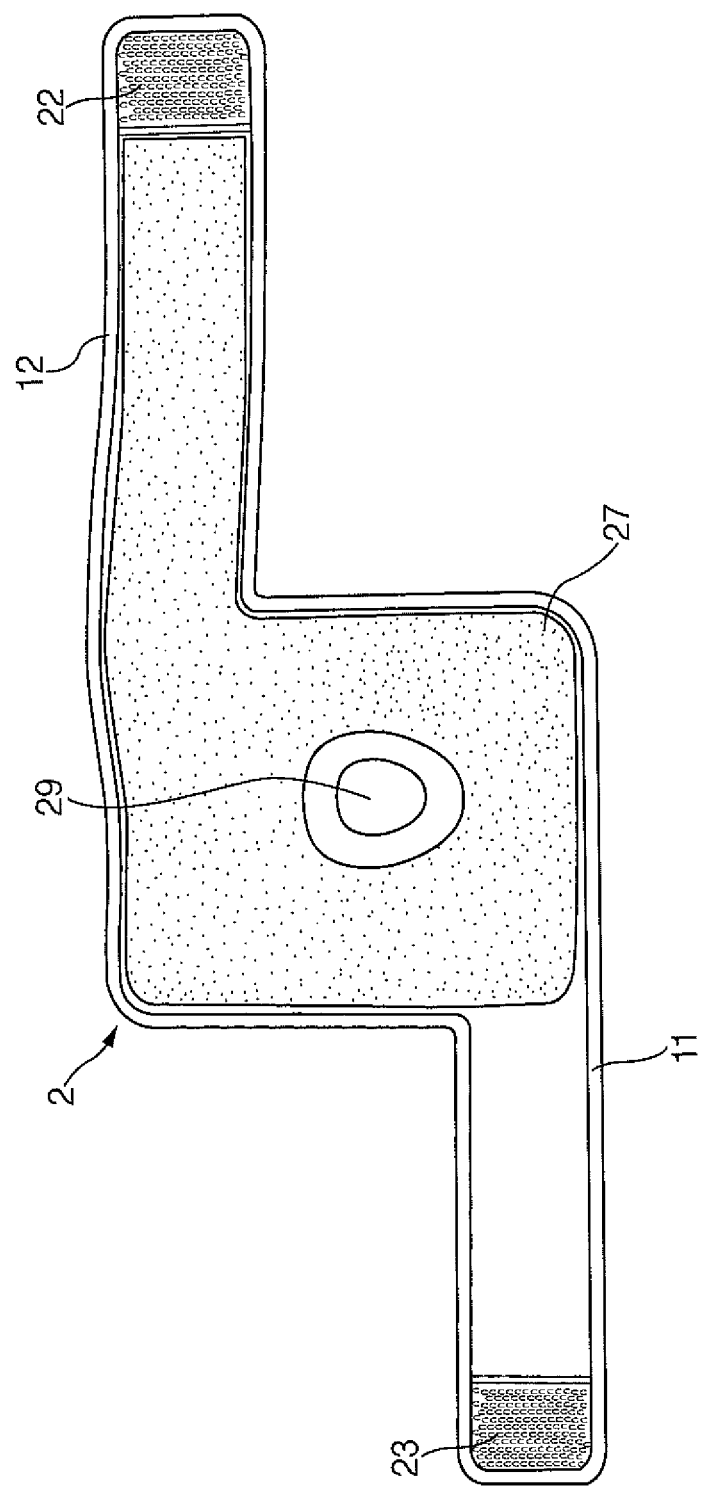
FIG. 10 is a diagrammatic rear view of the knee assembly in the foot support device shown in FIG. 9 with the knee assembly shown disengaged from the foot support device and removed from the patient and with the adjustable straps in the knee assembly shown in their fully unwrapped position.
Figure 11:
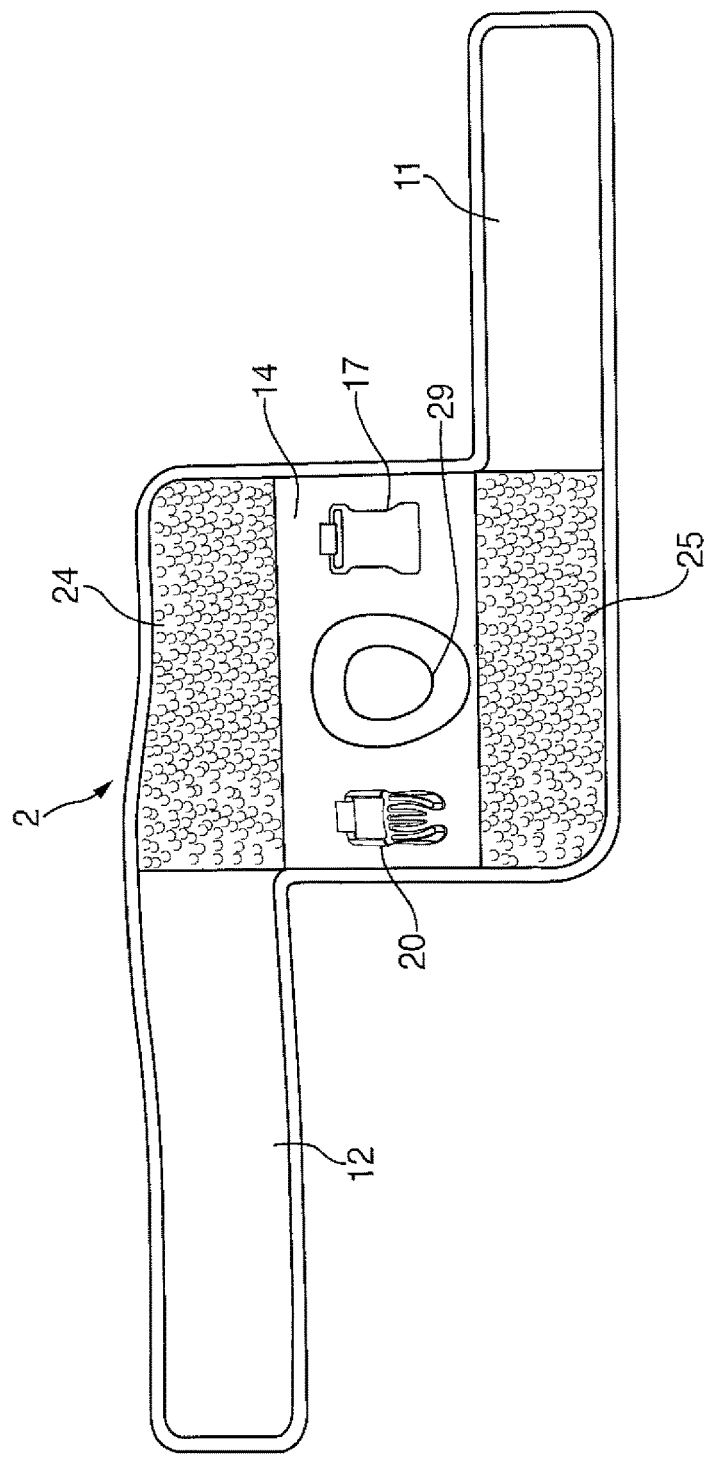
FIG. 11 is a diagrammatic front view of the knee assembly of the foot support device shown in FIG. 9 with the knee assembly shown disengaged from the foot support device and removed from the patient and with the adjustable straps in the knee assembly shown in their fully unwrapped position.

A first embodiment of the foot support device 10 of the present invention is shown in FIGS. 1-4 inclusive, comprising at least the following three main elements: (a) a foot assembly 1, (b) a Tension Assembly comprised of tension straps 3 and 4, and (c) a Knee Assembly 2 with the three main elements forming a single integrated unit. The Knee Assembly 2, as is shown in FIG. 1, is comprised of elastic material 14 composed preferably of a soft synthetic fabric, a securing adjustment strap 12 at the top of the Knee Assembly 2, a securing adjustment strap 11 at the bottom of the Knee Assembly 2, and two rigid buckles 7 and 8 affixed to the section 14 of elastic material on opposite sides of the knee assembly 2 in alignment with the rotatable joint of the knee. The elastic material 14 provides the foundation of Knee Assembly 2, forming a comfortable brace, which upon attachment to the leg, surrounds and engages the knee. The upper and lower securing adjustment straps 12 and 11 are part of the Knee Assembly 2 with the securing upper adjustment strap 12 located directly above the kneecap and the lower securing adjustment strap 12 located directly below the kneecap. The upper and lower securing adjustment straps 12 and 11 removably engage and disengage the Knee Assembly 2 to the leg. This is preferably accomplished using Velcro strips of material 24 and 25 (not shown 22 and 23) with a first set of strips of Velcro material (22 and 23 not shown) fixedly attached to the tips of both the upper and lower securing adjustment straps on one side thereof and a second set of Velcro strips 24 and 25 fixedly attached on a side of the Knee Assembly 2 opposing the corresponding locations of the first set of velcro strips as will be explained in greater detail in connection with the second embodiment of the invention and as shown in FIGS. 10 and 11. The Velcro strips function as velcro fasteners for manually engaging and disengaging the Knee Assembly 2 to the knee upon wrapping or unwrapping the securing adjustment straps 12 and 11 around the knee and engaging or disengaging the first and second set of Velcro strips to one another.

The rigid buckles 7 and 8 may each be composed of a metal loop in preferably a rectangular configuration having opposite open sides with one open side of each metal buckle 7 and 8 in an adjustable engagement with a free end of each tension strap 3 and 4 and with the other open side of each metal buckle 7 and 8 affixed to the Knee Assembly 2 on opposite sides thereof. The free end of each tension strap 3 and 4 may be looped in a conventional manner through one open side of each metal buckle 7 and 8 so that the position of attachment of each tension strap 3 and 4 to the rigid buckles 7 and 8 is manually adjustable. The opposite open side of each metal buckle 7 and 8 may be connected to the Knee Assembly 2 using two interconnecting strips of securing fabric 5 and 6 which may be directly stitched to the elastic material 14 of the Knee Assembly 2 so that the position of the rigid buckles 7 and 8 on opposite sides of the Knee Assembly 2 lie in alignment with the rotatable joint of the knee.

Each tension strap 3 and 4 is anchored to the knee assembly 2 at opposite sides of the rotatable joint of the knee through the rigid buckles 7 and 8 with the opposite end of each tension strap 3 and 4 connected together to form a single continuous tension strap extending from the Knee Assembly 2 on opposite sides of the knee and slides freely extending through a strap channel guide member 9 in the Foot Assembly 1 relative to the ball of the foot for providing continuous tension to the ball of the foot even when the leg is moved by the patient during treatment of the foot for plantar fasciitis as will be hereafter explained in greater detail. Tension in the continuous strap is controlled by adjustably tightening the tension strap [FIG. 1, member 3] in the rigid buckle 7 or by adjustably tightening the coupling of both tension strap 3 and 4 in the rigid buckles 7 and 8 respectively. Tension in member 3 is channeled through the rigid buckle member 7 for applying appropriate tension to dorsiflex the ball of the foot.

By anchoring the tension straps 3 and 4 to the opposite sides of the knee at a fulcrum point contiguous with the rotatable joint of the knee assures uniformity and consistency in tension in each of the tension straps 3 and 4 even if the patient is mobile. The tension applied by the tension straps 3 and 4 in the Foot Support Device 10 must remain substantially constant and consistent to therapeutically treat plantar fasciitis while simultaneously moving the leg or simultaneously walking. This is a result of the interconnected adjustable tension straps 3 and 4 which slide freely within the strap channel guide opening 13 of the strap channel guide member 9 in the Foot Assembly 1 relative to the ball of the foot so that as the patient moves the foot in treatment the interconnected tension straps 3 and 4 slide within the strap channel guide member 9 to maintain uniform and consistent dorsiflexion of the plantar fascia. This dynamic arrangement between the integrated Foot Assembly 1, Knee Assembly 2 and the tension straps 3 and 4 in the Tension Assembly is therefore critical if the patient, wearing the Foot Support Device 10, desires mobility while undergoing treatment for plantar fasciitis.

The Foot Assembly 1, comprises a sock 30 adapted to be worn over the foot with the strap channel guide member 9, attached to the sock 30 under the ball of the foot, providing a free sliding medium for tension straps 3 and 4 the single continuous tension strap, formed by the interconnected tension straps 3 and 4, through the strap channel guide opening 13 in the strap channel guide member 9 to dorsiflex the ball of the foot. The pressure applied by the tension straps 3 and 4 to the ball of the foot controls dorsiflexion of the plantar fascia. As long as pressure on both sides of the foot is maintained equal and tension in the straps 3 and 4 is maintained substantially constant, the ball of the foot can be dorsiflexed while simultaneously moving the leg thereby simultaneously allowing the leg to be mobile while at the same time controlling dorsiflexion of the plantar fascia in the foot. This is accomplished only when each tension straps 3 and 4 is anchored to the Knee Assembly 2 at a position, in substantial alignment with the rotatable joint of the knee, on opposite sides of the Knee Assembly 2, which assures that the tension applied by the tension straps 3 and 4 will be substantially uniform and constant.

It should be understood that the Tension Assembly in the subject invention requires only one tension strap 3 to be adjustably looped through a rigid buckle 7 and secured by securing material 5 to one side of the Knee Assembly 2 to form a point of connection between the tension strap 3 and the rigid buckle 7 with the location in alignment with the rotatable joint of the knee. The other tension strap 4 may be fixedly attached to the Knee Assembly 2 on the opposite side of the knee without the use of a rigid buckle 8 i.e., by means of a direct connection or another type of buckle or a coupling as used in the second embodiment of the present invention. Nevertheless, the point of connection between each tension strap 3 and 4 and the Knee Assembly 2 must still be in alignment with the rotatable joint of the knee. The use of two rigid buckles 7 and 8 secured to the Knee Assembly 2 on opposite sides of the knee with each rigid buckle connecting one end of each tension strap 3 and 4 to the Knee Assembly 2 at a location in alignment with the rotatable joint of the knee is one preferred way to assure that consistent tension will be applied to the ball of the foot in accordance with the present invention which will permit the patient to be mobile and move the leg under treatment. This arrangement also facilitates easy attachment and removal of the Tension Assembly tension straps 3 and 4 to and from the Knee Assembly 2.

Figure 3:
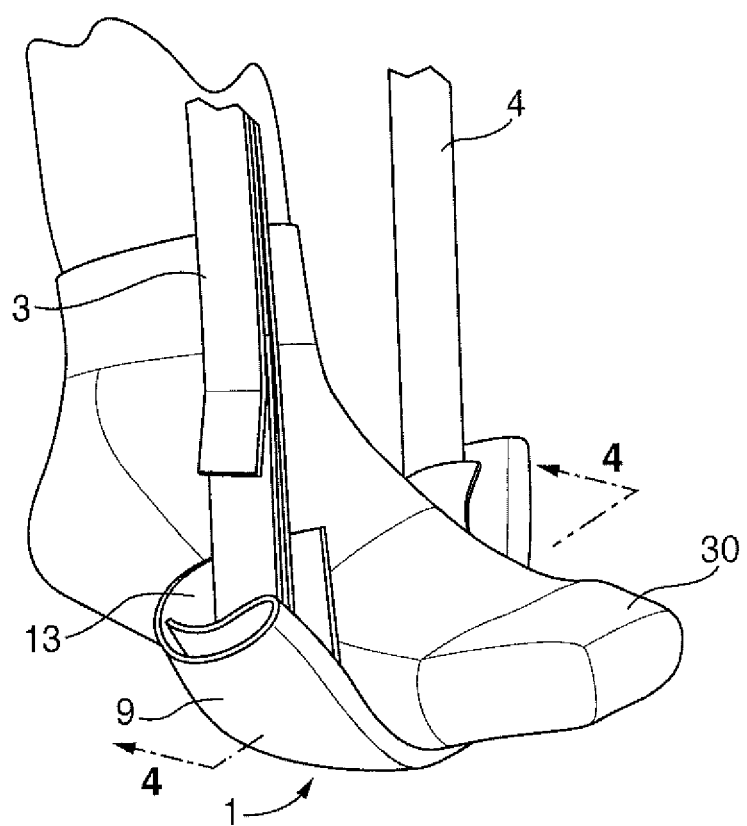
FIG. 3 is an enlarged perspective view of the first embodiment of the invention shown in FIG. 1 showing the arrangement of the foot assembly and tension assembly in the foot support device relative to the ball of the foot of the patient.
Figure 4:
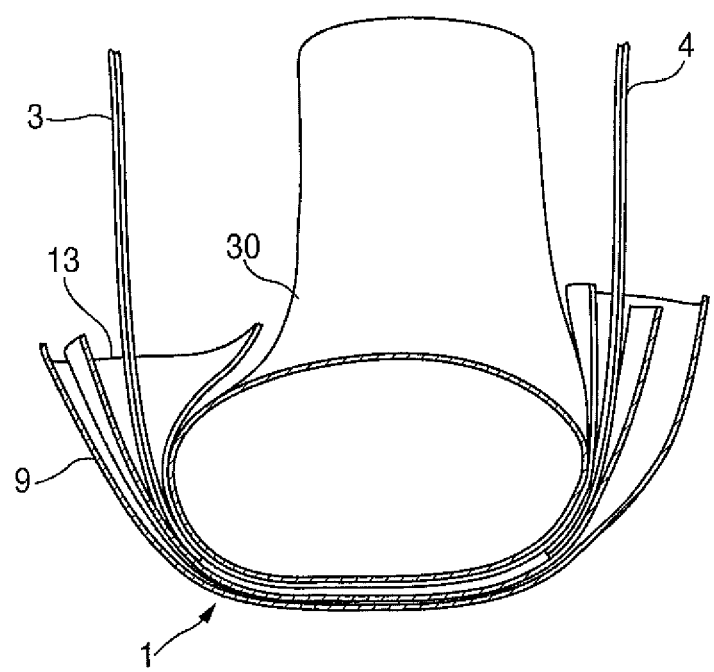
FIG. 4 is a front view of the foot support device shown in FIG. 2.

The Foot Assembly 1 illustrated in FIG. 3 comprises a sock 30 in combination with the strap channel guide member 9 and strap channel guide opening 13. The continuous strap, formed by the interconnected tension straps 3 and 4, slides freely, passing through the strap channel guide opening 13 in the strap channel guide member 9 to go from one side of the Knee Assembly 2 to a corresponding location on the opposite side of the Knee Assembly 2 in alignment with the rotatable joint of the knee. The strap channel guide member 9 is preferably attached to the bottom of the sock 30 so that the continuous loop of tension straps 3 and 4 will be guided through the strap channel guide opening 13 of the strap channel guide member 9 preferably under the ball of the foot and in a direction transverse to the arch which guarantees appropriate dorsiflexion of the plantar fascia. The strap channel guide member 9 may be fixed to the sock 30 with an adhesive or by stitching, or any other known method.

The sock 30 in addition to orienting the loop of tension straps 3 and 4 through the strap channel guide member 9 also assures that the Foot Assembly 1 is comfortable for the wearer and hygienic as it is easily washable. The strap channel guide member 9 must orient the direction of the continuous strap of tension straps 3 and 4 through the Foot Assembly 1 along a path directly under the ball of the foot to achieve consistent dorsiflexion of the plantar fascia. If a sock 30 were not used, the strap channel guide member 9 may readily be pulled away from the ball of the foot the minute pressure is applied to the loop of tension straps 3 and 4 and may cause damage to the toes or fail to maintain the loop of tension straps 3 and 4 in a fixed orientation relative to the arch of the foot to assure constant tension and thereby lose the ability to provide appropriate dorsiflexion of the plantar fascia during movement of the leg.

The use of a sock 30 prevents shifting of position of the loop of tension straps 3 and 4 relative to the ball of the foot. As long as the loop of tension straps 3 and 4 extends from a position on opposite sides of the Knee Assembly 2 in alignment with the rotatable joint of the knee and lies in a fixed position relative to the ball of the foot, applying consistent pressure to the ball of the foot which, in turn, guarantees consistent dorsiflexion to the plantar fascia while allowing the patient to be mobile. Accordingly, a guide member, such as strap channel guide member 9 is essential, to orient the strap of tension straps 3 and 4 to slide under the ball of the foot through the strap channel guide member 9 or alternatively, across the ball of the foot by locating the strap channel guide member 9 over the foot and preferably on the top of the sock 30. Either method will provide the comfort and mobility required in this embodiment of the invention.

A Foot Assembly 1 which includes a sock 30 increases the comfort of the user and by securing the strap channel guide member 9 in the Foot Assembly 1 to the bottom of the sock 30 and under the ball of the foot concentrates the tension force at the ball of the foot. The Foot Assembly 1 should preferably be made from materials that can be easily cleaned and will provide comfort to the user when the Foot Support Device 10 is attached to the leg while asleep or when sitting or walking.

As explained previously, the Tension Assembly comprises two linear tension straps 3 and 4 which are attached to each other to form one continuous strap which extends about the ball of the foot from the Foot Assembly 1 to the Knee Assembly 2. Each linear tension strap 3 and 4 is channeled through a rigid buckle 7 and 8 secured to the Knee Assembly 2. The user can tighten the tension strap 3 by pulling the tension strap 3 further through the rigid buckle 7 until a desired tension is achieved before securing the tension strap to the rigid buckle using, for example, a hook and loop fastener (not shown) which is then attached to tension strap 3. In reference to the embodiment shown in FIG. 2, the tension straps 3 and 4 are channeled onto the Knee Assembly via the buckles 7 and 8 at the side of the rotatable joint of the knee where they maintain controllable and consistent dorsiflexion of the plantar fascia in accordance with tension adjustment to the tension straps 3 and 4.

DETAILED DESCRIPTION OF THE SECOND EMBODIMENT OF THE INVENTION

Figure 5:
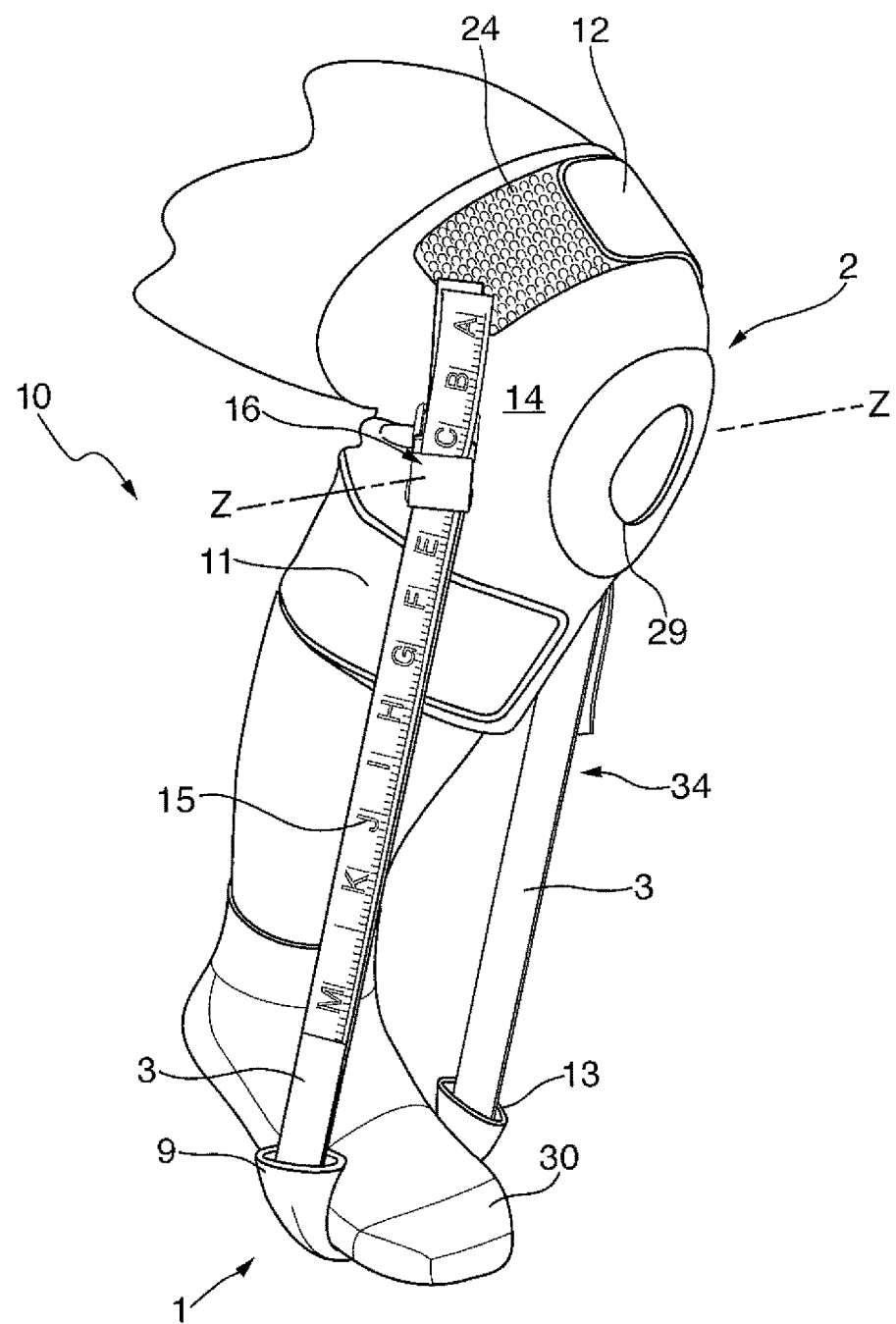
FIG. 5 illustrates a second embodiment of the foot support device of the present invention shown in perspective and attached to a leg of a patient.

The second embodiment of the present invention is shown in FIG. 5 through FIGS. 14A-14B inclusive, comprising at least the following three main elements: (a) a Foot Assembly 1, (b) a Tension Assembly 34 and (c) a Knee Assembly 2 with the three main elements forming a single integrated unit. The same reference numbers are used in the second embodiment to identify identical components used in the first embodiment. The Knee Assembly 2, as is shown in FIG. 5, includes elastic material 14 composed of soft stretchable polyurethane synthetic or similar type fabric, which upon attachment to the leg forms a brace surrounding the knee. The Knee Assembly 2 also includes an upper securing adjustment strap 12 and a lower securing adjustment strap 11 with the upper strap 12 located directly above the kneecap and the lower strap 11 located directly below the kneecap as in the first embodiment. As shown in FIG. 10, a Velcro fastener tip 22 is attached to the upper securing adjustment strap 12 on its underside at an outer end thereof and Velcro fastener tip 23 is attached to the lower securing adjustment strap 11 on its underside at an outer end diametrically opposite the location of the Velcro fastener tip 22. The Knee Assembly 2, in the second embodiment also includes a non-slip liner 27 which serves to stabilize the Knee Assembly 2, as shown in FIG. 10, is attached to the elastic material 14 on its underside surface and further includes Velcro fastener sections 24 and 25 on opposite ends of the non-slip liner 27. The Knee Assembly 2 is removably attached to the user's leg, by properly fastening both upper and lower securing adjustment straps 12 and 11 to the Knee Assembly 2, positioning the alignment opening 29 of the Knee Assembly 2 with the kneecap to establish proper alignment of the Knee Assembly 2 on the knee of the leg and attaching the velcro fastener tips 22 and 23 to the velcro fastener sections 24 and 25. The placement of the fastener velcro tips 22 and 23 relative to the position of the velcro fastener sections 24 and 25 on the circumference of the knee allows the wearer to adjust the degree of tightness of the upper and lower securing adjustment straps 12 and 11 and the Knee Assembly 2 to the knee of the user's leg. The Knee Assembly 2 is readily removed from the leg upon disengaging the Velcro fastener tips 22 and 23 on the upper and lower securing adjustment straps 12 and 11 from the velcro fastener sections 24 and 25.

Figure 9:
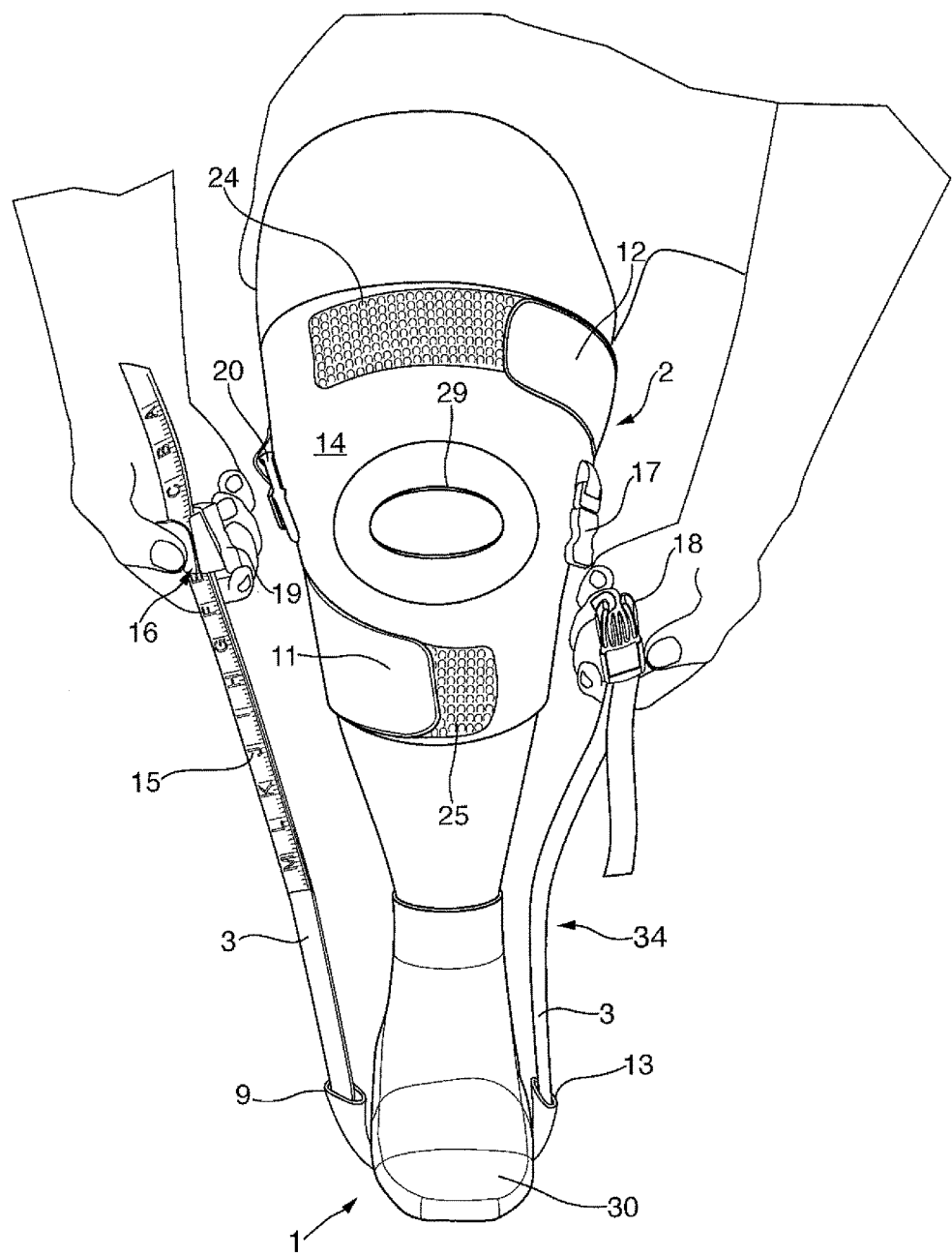
FIG. 9 is an exploded view in perspective of the foot support device shown in FIG. 6 showing how the tension assembly is engaged and disengaged from the knee assembly in the foot support device.

The present invention employs coupling members for readily engaging and disengaging the Tension Assembly 34 to and from the Knee Assembly 2 which in the first embodiment corresponds to the rigid buckles 7 and 8 and in the second embodiment preferably comprises two pairs of conventional male and female quick connects, 17, 18 and 19, 20, preferably of the bayonet type, as shown in FIGS. 13A and 13B. A male quick connect member 20 and a female quick connect member 17 are attached to the Knee Assembly 2 in an arrangement with each located on opposite sides of the central opening 29 of the Knee Assembly 2, as shown in FIGS. 9 and 11, in a position such that when the Foot Support Device 10 is attached to the leg to be treated the central opening 29 in the knee assembly 2 is aligned to expose the kneecap. The connection point between the pair of quick connect members 20 and 19 on one side of the knee and the connection point between the pair of quick connect members 17 and 18 on the opposite side of the knee are in substantial alignment with the axis Z-Z extending through the rotatable joint of the knee. The quick connect members 20 and 19 are preferably located on opposite sides of the central opening 29 adjacent the Velcro sections 24 and 25 as shown in FIG. 11 and may be affixed to the Knee Assembly 2 by stitching or with an adhesive.

The Tension Assembly 34 as shown in FIG. 12 comprises a single tension strap 3 with one end thereof attached to the male quick connect member 18 and with the other end of the tension strap 3 attached to the female quick connect member 19 as is shown in FIG. 9. The male quick connect member 18 engages the female quick connect member 17 on one side of the Knee Assembly 2 and the female quick connect member 19 engages the male quick connect member 20 on the opposite side of the knee assembly 2. The Tension Assembly 34 further includes a clamp assembly 16 which is fixedly mounted upon the female quick connect member 19 as shown in FIG. 9 and FIG. 14A respectively. The strap 3 in the Tension Assembly 34 is fed through the clamp assembly 16 which comprises an adjustable strap clamp 21 and a manually operated locking lever 26, as shown in FIGS. 14A and 14B. The tension strap 3 is locked into a set position by depressing the locking lever 26 into the strap clamp 21 of the clamp assembly 16. The clamp assembly 16 is mounted upon and affixed to the female quick connect member 19 by adhesion or by other suitable method. The Tension Assembly 34 is comprised of only the single tension strap 3 which forms a continuous loop between the Knee Assembly 2 and the Foot Assembly 1. A gradient reference system 15 is affixed to the tension strap 3, preferably on the right side of the knee, for establishing reference settings points on the tension strap corresponding to tension settings of the tension strap 3 which readily enables the user to set and recall settings of the tension strap 3 for maintaining consistent dorsiflexion to the foot in the treatment of Plantar Fasciitis.

The Foot Assembly 1, is comprised of a sock 30, and a strap channel guide member 9 preferably attached to the bottom of the sock 30 using an adhesive or by stitching the sock 30 to the strap channel guide member 9, with the strap channel guide member 9 preferably oriented in a direction across the ball of the foot. The strap channel guide member 9, maintains orientation of the tension strap 3 relative to the ball of the foot and has an opening 13 extending therethrough which allows the tension strap 3 to slide freely to adjust position within the opening 13 of the strap channel guide member 9 such that consistent tension is applied from the tension strap 3 to the ball of the foot for the purpose of simultaneously dorsiflexing the plantar fascia while the patient is mobile, i.e., is moving the leg under treatment. The sliding motion of the tension strap 3 through the strap channel guide member 9 automatically equalizes the pressure on both sides of the foot which allows for mobility of the leg while consistent balanced tension is being applied to the foot for the proper treatment of plantar fasciitis. By attaching the strap channel guide member 9 to the bottom of the sock 30 under the ball of the foot guarantees that the tension strap 3 will always be connected to the ball of the foot and in a proper orientation to apply appropriate dorsiflexion of the plantar fascia. The strap channel guide member 9 also protects the ankle and the foot from unnecessary torqueing and twisting as tension is adjusted in the tension member 3, as a result of the tension member 3 adjustably sliding in the strap channel guide member 9. This automatically keeps the tension force equalized on both sides of the foot.

The non-slip liner 27 in the Knee Assembly 2 prevents slippage and movement of the Knee Assembly 2 upon attachment of the Foot Support Device 10 to the leg and sets the Knee Assembly 2 in place which stabilizes the Tension Assembly 34. When the foot support device 10 is in use the quick connector members 17, 18, 19 and 20 anchor the Tension Assembly 34 to the Knee Assembly for providing consistent tension to the ball of the foot even during movement of the leg. The quick connector members 17, 18, 19 and 20 also allow the user to quickly release the Tension Assembly 34 from the Knee Assembly 2 when the treatment session is completed. The clamp assembly 16 enables the wearer to set the tension of the tension strap 3 and the pressure applied to the plantar fascia by adjusting the position in which the tension strap 3 is locked in the clamp assembly 16. The setting of the locked position of the tension strap 3 in the clamp assembly 16 provides adjustable control of the proper tension setting for dorsiflexing the foot. The gradient reference system 15 is a visual aid enabling the wearer to select an alphabetical setting of tension and to inform the wearer as to the progress gained through usage, so that the wearer can consistently set and maintain the tension required to optimize dorsiflexion of the plantar fascia.

Figure 6:
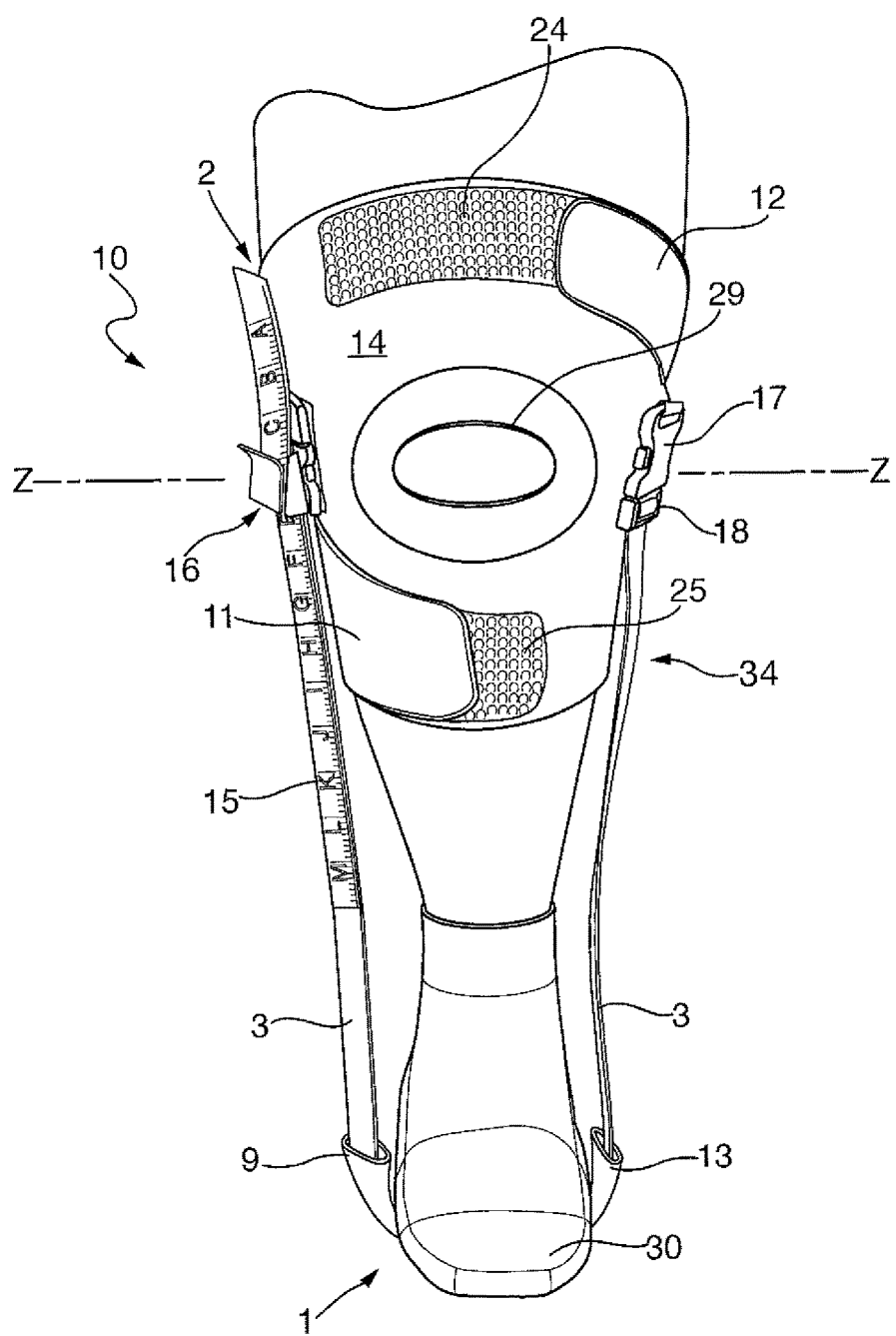
FIG. 6 is another perspective view of the second embodiment of the foot support device as shown in FIG. 5 with the foot support device shown rotated ninety degrees from the position shown in FIG. 5.
Figure 7:
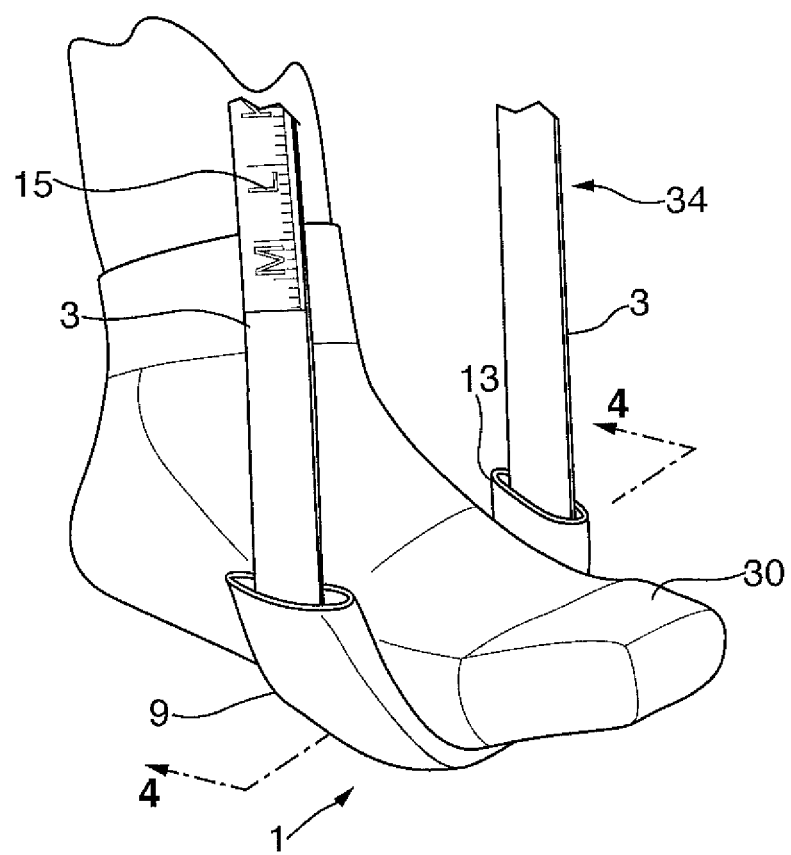
FIG. 7 is an enlarged perspective view of the second embodiment of the present invention showing the arrangement of the foot assembly and tension assembly in the foot support device in FIG. 5 relative to the ball of the foot of the patient.
Figure 8:
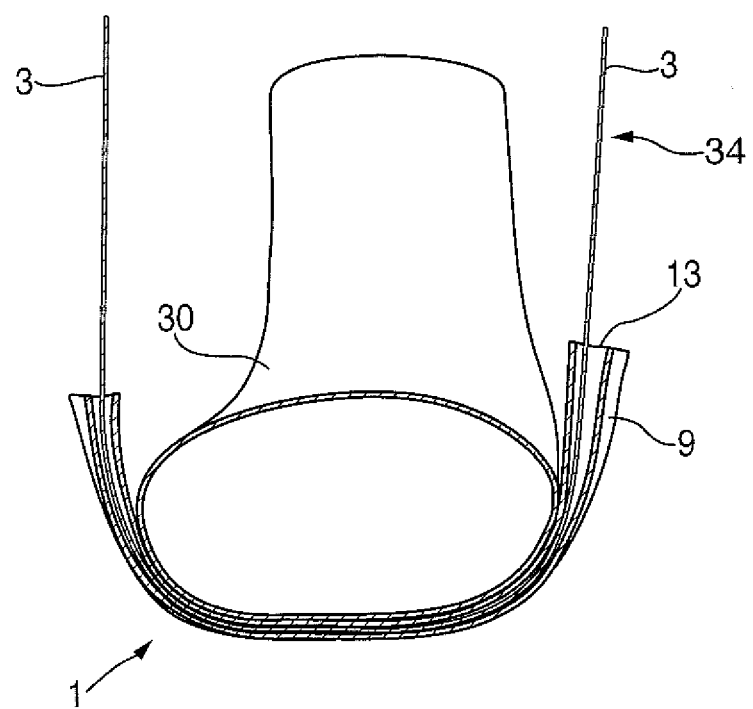
FIG. 8 is a front view of the foot support device shown in FIG. 5.

The connection points formed upon engagement of the quick connect members 20 and 17 in the Knee Assembly 2 to the quick connect members 19 and 18 affixed to the tension strap 3 are located on opposite sides of the knee in alignment with the axis Z-Z extending through the rotatable joint in the knee as shown in FIG. 6. Because the quick connect members 17 and 20, attached to the Knee Assembly 2, are located in alignment with the rotatable joint of the knee the tension force from the tension strap 3 is transferred from the rotatable joint of the knee to the ball of the foot. Thus, when the Foot Support Device 10 is in use, the tension force transferred from the rotatable joint of the knee provides consistent dorsiflexion of the plantar fascia even while the patient is mobile and the leg is being moved. The quick connectors 18 and 19 on each end of the tension strap 3 enable the wearer to easily detach the Tension Assembly 34 and the Knee Assembly 2 upon completion of the treatment for plantar fasciitis. The wearer then removes the sock 30 and the Foot Assembly 1 followed by the removal of Knee Assembly 2 from the leg.

By using a sock 30 for orienting the tension strap 3 through the strap channel guide member 9, assures that the Foot Assembly 1 will be comfortable to the wearer. Moreover, the sock 30 is easily washable once the Tension Assembly strap 3 is disengaged from the strap channel guide member 9 and removed from the leg. The comfort of a sock 30 allows the patient the mobility to easily move the foot with no discomfort, and to more comfortably walk or sleep with the Foot Support Device 10 attached to the leg.

It should be understood by that many different foot assemblies are possible. Although the tension strap 3 should be fed through the opening 13 in the strap channel guide member 9 so that the tension strap 3 may slide freely in the strap channel guide member 9 can be oriented relative to the ball of the foot by placement across the ball of the foot or under the ball of the foot and the strap channel guide member 9 may be affixed to the top of the sock 30 provided the tension strap 3 is able to slide through the guide member relative to the ball of the foot. Either method would provide comfort and mobility to the patient. Nevertheless, it is preferred for the strap channel guide member 9 to be secured to the bottom of the sock 30 under the ball of the foot because this arrangement concentrates the tension force at the ball of the foot. It should be understood that the sock 30 can be represented by any soft material in any configuration which can be affixed to the foot to which the guide member 9 can be secured at a location preferably under the ball of the foot. The Foot Assembly 1 is composed of soft materials that can be easily cleaned, allow mobility and provide comfort while sleeping, sitting or walking. In fact it is preferred that all of the elements of the Foot Support Device 10 including the Knee Assembly 2, Foot Assembly 1, and Tension Assembly 34, be composed of soft materials which are comfortable, washable, and portable as the device is easily packed for travel or transport for convenience which encourages use and consequently enhances the chance for improvement of the plantar fasciitis condition.

It is preferable that the tension strap 3 be a linear continuous strap and should extend through the Foot Assembly 1 to the Knee Assembly 2 with the tension strap 3 on each side of Tension Assembly 34 secured to the Knee Assembly 2 to form connection points, represented by engagement of the quick connect members 17, 18, 19 and 20 between the Tension Assembly 34 and the Knee Assembly 2. In FIG. 6 the tension strap 3 on the left side of the knee is shown threaded through the male quick connect member 18 for engagement with the female quick connect 17 attached to the Knee Assembly 2. Only the tension strap 3 on the right side of the knee which extends through the clamp assembly 16 is adjustable by pulling the tension strap 3 upward through the strap clamp 21 in the clamp assembly 16 for controlling tension and resultant dorsiflexion of the foot before securing the strap clamp 21 in place by snapping the locking lever 26 to the closed position to secure tension strap 3 at a desired setting. Gradient reference system 15, in Tension Assembly 34, is the visual alphabetic device that allows the wearer to quickly recall or select the desired setting that determines the appropriate tension on the plantar fascia by closing the strap clamp 21 in the clamp assembly 16 at the appropriate tension setting for the tension strap 3.

It should be understood that the foregoing is illustrative and not limiting, and that obvious modifications may be made by those skilled in the art without departing from the essence of the invention.

TABLE OF KEY COMPONENT REFERENCE NUMBERS FOR CIP DRAWINGS

| Number | Description |
|---|---|
| 01 | Foot Assembly |
| 02 | Knee Assembly |
| 03 | Tension Strap |
| 04 | Tension Strap |
| 05 | Securing Material |
| 06 | Securing Material |
| 07 | Rigid Loop Buckle |
| 08 | Rigid Loop Buckle |
| 09 | Strap Channel Guide Member |
| 10 | Foot support device |
| 11 | Lower Securing Adjustment Strap for Knee assembly |
| 12 | Upper Securing Adjustment Strap for Knee assembly |
| 13 | Strap Channel Guide Opening |
| 14 | Knee Assembly Elastic Material |
| 15 | Gradient Reference System |
| 16 | Clamp Assembly |
| 17 | Female Quick Connect |
| 18 | Male Quick Connect |
| 19 | Female Quick Connect |

TABLE OF KEY COMPONENT REFERENCE NUMBERS FOR CIP DRAWINGS -continued

| Number | Description |
|---|---|
| 20 | Male Quick Connect |
| 21 | Tension Strap Adjustment Clamp |
| 22 | Velcro Fastener Tip [Inner Side Knee Assembly Securing Strap] |
| 23 | Velcro Fastener Tip [Inner Side Knee Assembly Securing Strap] |
| 24 | Velcro Fastener Tip [Outer Side Knee Assembly Securing Strap] |
| 25 | Velcro Fastener Tip [Outer Side Knee Assembly Securing Strap] |
| 26 | Clamp Control Lever |
| 27 | Non Slip Liner in Knee Assembly |
| 28 | <Not Used> |
| 29 | Knee Assembly Alignment Opening |
| 30 | Sock |
| 31 | <Not Used> |
| 32 | <Not Used> |
| 33 | <Not Used> |
| 34 | Tension Assembly $2^{nd}$ embodiment |

What is claimed is:

1. A foot support device, adapted for attachment to a leg of a wearer, for therapeutically treating plantar fasciitis in a foot in said leg of said wearer by dynamically controlling and maintaining dorsiflexion of the plantar fascia even if the wearer is mobile during treatment, comprising:
 a foot assembly comprising a sock, adapted for placement over the foot in said leg to undergo treatment, and a guide member affixed to the sock on the underside of the foot at a location proximate a ball of the foot between the toes and the arch with said guide member having an opening forming a channel extending through the guide member in an orientation lying substantially transverse to the ball of the foot;
 a knee assembly comprising a first and second adjustable strap in a relationship above and below the kneecap of the knee in said leg, and a material section interconnecting the first adjustable strap to the second adjustable strap such that upon attachment of the foot support device to said leg the knee assembly forms a brace for the knee which engages and surrounds the knee,
 a tension assembly comprising a tension strap having open ends with the tension strap extending through the opening in said guide member such that the tension strap can freely slide within the channel formed in the opening in said guide member, with said foot assembly, knee assembly and tension assembly forming a single integrated unit upon attachment of the foot support device to said leg, and
 wherein said foot support device further comprises;
 coupling members connecting the open ends of the tension strap in the tension assembly to the knee assembly, at points of connection on the knee assembly located on opposite sides of the knee in approximate alignment with a horizontal axis extending through the rotatable joint of the knee, such that the tension strap is held in tension while simultaneously forming a continuous loop extending from one open end of the tension strap on one side of the knee assembly through the channel formed in said guide member on the underside of the foot to the opposite open end of the tension strap on the opposite side of said knee assembly whereby
 said tension strap maintains dorsiflexion of the plantar fascia in the foot of the leg undergoing treatment, at least to a minimum degree, even when the leg or foot of the wearer is mobile during treatment.

2. The device of claim 1 wherein said coupling members comprise buckles for interconnecting each open end of said strap to said knee assembly at said points of connection to said knee assembly at opposite sides of the knee.

3. The device of claim 1 wherein said coupling members comprise male and female quick connect members including a first pair of quick connect members consisting of a male and female quick connect member attached at points of contact to the knee assembly located on each opposite side of the knee in substantial alignment with an axis extending through the rotatable joint of the knee and a second pair of quick connect members consisting of a female and male quick connect member attached to the opposite ends of the tension strap in opposing relationship to the first pair.

4. The device of claim 3 further comprising a clamp assembly for manually adjusting the tension in said tension strap with said clamp assembly being mounted on one of said coupling members and having a manually adjustable locking lever and a strap clamp through which the tension strap extends with the manually adjustable locking lever having one position for opening the strap clamp to allow the tension strap to be manually adjusted to change the degree of tension in said tension strap and having another position for locking the strap in place in the strap clamp so as to fix the tension in the tension strap to a desired minimum tension.

5. The device of claim 4 further comprising a gradient reference system mounted to said strap to provide a visual guide to the wearer of the foot support device of the tension setting in said tension strap or for readjusting the tension setting.

6. The device of claim 3 wherein said knee assembly comprises a non-slip liner on the inner surface of the knee assembly facing the knee to stabilize the knee assembly when attached to the leg to be treated.

* * * * *